United States Patent
Shim (10) Patent No.: US 7,161,013 B2
(45) Date of Patent: Jan. 9, 2007

(54) TERTHIOPHENE-3-CARBOXYLIC ACID COMPOUND AND FABRICATING METHOD THEREOF, FUNCTIONALIZED CONDUCTIVE TERTHIOPHENE POLYMER WITH THE COMPOUND AS A MONOMER, PROCESS FOR DNA HYBRIDIZATION DETECTION USING THE POLYMER, AND FABRICATING METHOD OF PROBE DNA

(75) Inventor: Yoon-Bo Shim, Pusan (KR)

(73) Assignee: Pusan National University Industry-University Cooperation Foundation, Pusan (KR)

( * ) Notice: Subject to any disclaimer, the term of this patent is extended or adjusted under 35 U.S.C. 154(b) by 433 days.

(21) Appl. No.: 10/489,183

(22) PCT Filed: Sep. 11, 2002

(86) PCT No.: PCT/KR02/01706

§ 371 (c)(1),
(2), (4) Date: Mar. 10, 2004

(87) PCT Pub. No.: WO03/024954

PCT Pub. Date: Mar. 27, 2003

(65) Prior Publication Data

US 2005/0064415 A1  Mar. 24, 2005

(30) Foreign Application Priority Data

Sep. 12, 2001  (KR) ...................... 10-2001-0056045

(51) Int. Cl.
*C07D 409/00* (2006.01)

(52) U.S. Cl. ....................................................... 549/59

(58) Field of Classification Search ................... 549/59
See application file for complete search history.

(56) References Cited

U.S. PATENT DOCUMENTS

| | | | | | |
|---|---|---|---|---|---|
| 3,050,442 | A | * | 8/1962 | Bijloo | 514/444 |
| 4,691,005 | A | * | 9/1987 | Sato et al. | 528/380 |
| 4,937,256 | A | * | 6/1990 | Kober et al. | 514/444 |
| 5,045,563 | A | * | 9/1991 | Morand et al. | 514/444 |
| 5,578,636 | A | * | 11/1996 | Chang et al. | 514/444 |
| 5,734,065 | A | * | 3/1998 | Saika | 549/59 |
| 5,741,811 | A | * | 4/1998 | Chang et al. | 514/444 |
| 6,414,164 | B1 | * | 7/2002 | Afzali-Ardakani et al. | 549/59 |
| 6,716,995 | B1 | * | 4/2004 | Huang et al. | 549/62 |
| 6,825,358 | B1 | * | 11/2004 | Afzali-Ardakani et al. | 549/59 |
| 6,878,801 | B1 | * | 4/2005 | Fujiki et al. | 528/380 |
| 6,936,190 | B1 | * | 8/2005 | Yoshida | 252/511 |
| 7,015,336 | B1 | * | 3/2006 | Reed et al. | 549/59 |

* cited by examiner

*Primary Examiner*—Deborah C. Lambkin
(74) *Attorney, Agent, or Firm*—GWiPS (57) ABSTRACT

A novel terthiophene-3-carboxylic acid compound is disclosed that a functionalized conductive terthiophene polymer having carboxylic groups produced in an electrochemical method using the compound as a monomer and a novel process for detecting DNA hybridization through impedance measurement using the polymer. In addition, a method for manufacturing a probe DNA used in the process for detecting DNA hybridization is provided. Since the process can detect DNA hybridization using impedance change, without the use of any indicator, small-sized sensor systems which measure impedance in a particular frequency range can be fabricated. The systems are applicable to portable sensors for identifying DNA sequence hybridization for clinical examination and disease diagnosis. Further, the process has an excellent selectivity of complementary sequences to mismatched sequences.

7 Claims, 5 Drawing Sheets

TERTHIOPHENE-3-CARBOXYLIC ACID COMPOUND AND FABRICATING METHOD THEREOF, FUNCTIONALIZED CONDUCTIVE TERTHIOPHENE POLYMER WITH THE COMPOUND AS A MONOMER, PROCESS FOR DNA HYBRIDIZATION DETECTION USING THE POLYMER, AND FABRICATING METHOD OF PROBE DNA

BACKGROUND OF THE INVENTION

1. Field of the Invention

The present invention relates to a novel process for detecting DNA hybridization through impedance measurement using a novel conductive polymer in the DNA biosensor and electrochemical biosensor fields and more particularly to a novel process for detecting DNA hybridization by preparing a novel 3'-carboxyl-5,2';5',2"-terthiophene compound; producing a functionalized conductive terthiophene polymer through an electrochemical polymerization using the compound as a monomer on a glassy carbon electrode; immobilizing a probe DNA (or oligonucleotide) onto the polymer and measuring the impedance before and after a hybridization with a target DNA (or oligonucleotide).

2. Related Prior Art

Recently, a need has developed for apparatuses capable of continuously and selectively detecting biological molecules in the biotechnology and medical diagnostic fields. In particular, special attention has been paid to the development of electrochemical biodetectors or biosensors based on DNA hybridization, interactions among drugs and carcinogenic substances and DNAs, and special DNA interactions including DNA damage in the electrochemical detection of nucleic acid. Among these sensors, a variety of DNA sensors have been used to detect DNA sequences, toxic compounds and trace organic compounds. In particular, a hybridization detection method for DNA sequences is recognized as one of most reliable methods in terms of its broad applicability to the genome.

In connection with DNA hybridization detection, some conventional methods for detecting DNA hybridization are known. For example, a method for optically measuring the intensity of fluorescence after hybridizing an immobilized probe DNA with a fluorescent substance(dye)-labeled target DNA (or oligonucleotide), is reported [see, Physicochemical and Engineering Aspects, 2000, 175, 147–152; Analytica Acta, 1997, 350, 51–58; Anal. Chem. 1994, 66, 3379–3383].

A method for measuring the redox of an indicator to detect DNA hybridization is also reported [see, Anal. Chem. 1996, 68, 2629–2634; Anal. Chem. 1994, 66, 3830–3833; Anal. Chem. 2000, 72, 1334–1341]. The method comprises hybridizing an immobilized probe DNA with a target DNA and reacting the hybridized DNAs with the indicator so that the indicator is intercalated into the double-stranded DNA.

Further, disclosed is a method for measuring frequency change using a quartz crystal microbalance (QCM) when a probe DNA immobilized onto the surface of electrode is reacted with a target DNA [see, Biointerfaces, 1998, 10, 199–204; J. Am. Chem. Soc., 1992, 114, 8299–8300].

Further, a method for measuring a potential shift and current change in the redox wave of a conductive polymer (polypyrrole probe) when a probe DNA immobilized onto the conductive polymer is reacted with a target DNA, is disclosed [see, J. Am. Chem. Soc., 1997, 119, 7388–7389; Synthetic Metals, 1999, 100, 89–94].

However, there is a disadvantage in that when a target DNA is labeled with an indicator, the sample preparation is complicated. In addition, when the indicator is inserted after hybridization, time required for experimental steps become long and thus industrially disadvantageous.

In the case of the above-mentioned optical method or the method using QCM, since the measuring instruments used in these methods are huge and expensive, it is necessary for experienced personnel to manage them, as well as the fact that they are unsuitable for portable equipment. In the electrochemical method using a redox indicator, since the degree of hybridization depends on the sensitivity of the indicator, the method's sensitivity and selectivity are problematic.

Further, in the case of the method measuring a redox wave of a polymer, the method is inapplicable to portable sensors.

Therefore, there is a need for a portable DNA sensor which can directly detect DNA hybridization without the use of an indicator thereby shortening the time required in the experiment and which even an inexperienced person can easily identify within a short time whether or not DNA hybridization has occurred.

Thus, the present inventors have earnestly and widely researched the above-mentioned problems in the conventional DNA hybridization detection and have found that when measuring impedance before and after hybridization using a functionalized conductive terthiophene polymer with a novel terthiophene-3-carboxylic acid compound as a monomer, DNA hybridization can be directly detected and as a result they accomplished the present invention.

SUMMARY OF THE INVENTION

Therefore, it is an object of the present invention to provide a novel compound 3'-carboxyl-5,2';5',2"-terthiophene.

It is another object of the present invention to provide a functionalized conductive terthiophene polymer produced using the 3'-carboxyl-5,2';5',2"-terthiophene compound as a monomer.

It is another object of the present invention to provide a novel process for detecting DNA hybridization by immobilizing a probe DNA (or oligonucleotide) onto the polymer followed by a method for measuring impedance before and after DNA hybridization.

It is yet another object of the present invention to provide a method for manufacturing the probe DNA (or oligonucleotide).

The functionalized conductive terthiophene polymer according to the present invention is produced by obtaining 3-cyanoterthiophene from 3-bromoterthiophene as a starting material, hydrolyzing the 3-cyanoterthiophene to prepare 3'-carboxyl-5,2';5',2"-terthiophene and electrochemically polymerizing the prepared 3'-carboxyl-5,2';5',2"-terthiophene as a monomer.

The process for detecting DNA hybridization according to the present invention comprises the steps of: producing the functionalized conductive terthiophene polymer through an electrochemical polymerization using the terthiophene compound on a glassy carbon electrode, thereby modifying the carbon electrode with the polymer; immobilizing a probe DNA (or oligonucleotide) onto the conductive polymer and measuring impedance before and after a hybridization with a target DNA (or oligonucleotide).

The probe DNA (or oligonucleotide) used in the process for detecting DNA hybridization is manufactured by binding an amine-bound alkyl group to the 5'-end of a DNA (or oligonucleotide).

BRIEF DESCRIPTION OF THE DRAWINGS

The foregoing and other objects, features and advantages of the present invention will become more apparent from the following detailed description when taken in conjunction with the accompanying drawings in which.

DETAILED DESCRIPTIONS OF THE PREFERRED EMBODIMENT

Hereinafter, the present invention will be explained in more detail.

DNA consists of two strands which form a double helical structure. An ssDNA (single-stranded DNA) binds with another ssDNA having a base sequence complementary to each other to form a double strand. This process is referred to as hybridization. DNA hybridization detection is a technique determining the differences before and after hybridization when a single-stranded probe DNA immobilized onto the surface of solid substrate is hybridized with a target DNA complementary to the probe DNA.

The process for detecting DNA hybridization according to the present invention electrochemically detects DNA hybridization by determining the difference in the impedance before and after hybridization using the functionalized conductive terthiophene polymer.

The 3'-carboxyl-5,2';5',2"-terthiophene compound according to the present invention is represented by the following formula 1:

The functionalized conductive terthiophene polymer according to the present invention is produced using the 3'-carboxyl-5,2';5',2"-terthiophene compound as a monomer. The terthiophene polymer has conductivity due to its chemical structural property.

Specifically, the functionalized conductive terthiophene polymer according to the present invention is produced as follows: first, 3-bromoterthiophene as a starting material is reacted with copper cyanide (CuCN) to obtain 3-cyanoterthiophene, represented by the following formula 2:

3-cyanoterthiophene thus obtained has a melting point of 83° C. and a molecular weight of 272.9736 g/mol. Subsequently, 3-cyanoterthiophene is hydrolyzed in the presence of potassium hydroxide-ethoxyethanol to prepare 3'-carboxyl-5,2';5',2"-terthiophene of formula 1. 3'-carboxyl-5,2'; 5',2"-terthiophene has a melting point of 193° C. and a molecular weight of 292.4002 g/mol. The functionalized conductive terthiophene polymer according to the present invention is represented by the following formula 3:

The terthiophene polymer is produced in an electrochemical method which synthesizes the polymer using 3'-carboxyl-5,2';5',2"-terthiophene as a monomer on the surface of an electrode in accordance with cyclic voltammetry method. The conductive polymer thus prepared has a reddish brown color.

The process for detecting DNA hybridization using the functionalized conductive polymer comprises the steps of: dissolving 3'-carboxyl-5,2';5',2"-terthiophene in a non-aqueous solvent; producing the conductive terthiophene polymer having carboxylic groups on the surface of an electrode in an electrochemical method and modifying the polymer; immobilizing a probe DNA (or oligonucleotide) amino-modified at its 5'-end using 1-ethyl-3-(3-dimethylaminopropyl) carbodiimide (EDAC) onto the polymer; and measuring impedance before and after DNA hybridization.

The electrode used herein is made of glassy carbon and gold. The terthiophene polymer is electrochemically produced and modified on the electrode surface in accordance with cyclic voltammetry method, and the probe DNA (or oligonucleotide) is chemically combined to the carboxylic groups of the polymer. The probe DNA (or oligonucleotide) used in the process for detecting DNA hybridization according to the present invention includes those corresponding to a target DNA (or oligonucleotide), and is preferably a 19-mer oligonucleotide. The probe DNA (or oligonucleotide) is a DNA (or oligonucleotide) modified with an amino group at its 5'-end, which is manufactured by binding an alkyl group having from 3 to 10 carbon atoms, preferably 6 carbon atoms, to the 5'-end of DNA having base sequences with a certain length, and then combining an amine to the alkyl group using 1-ethyl-3-(3-dimethylaminopropyl)carbodiimide (EDAC) to modify the 5'-end into an amino group.

A specific example of the DNA is $NH_2$—$C_6$-5'-CTCCT-GTGGAGAAGTCTGC-3'. Impedance measurement is performed at a frequency ranging from 10 Hz to 100 kHz, and preferably at a frequency of about 1 kHz.

In order to detect DNA hybridization in accordance with the present invention, a DNA base sequence from patients suffering from sickle cell anemia is used. First, a single-stranded probe of the DNA base sequence is immobilized onto the electrode surface. Subsequently, target DNA base sequences (Sequence B: 3'-GAG GACACCTCTTCA-GACG-5', Sequence C: 3'-GAGGACTCCTCTTCAGACG-5', Sequence D: 3'-CTGGACACCTCTTCAGACG-5', Sequence E: 3'-CCTAGTCTACAGGTCACTA-5'), respectively, complementary to the single-stranded probe are hybridized in a phosphate buffer. Finally, impedance before and after hybridization is measured. Differences between log values of the measured impedance before and after hybridization are calculated. The target DNA base sequences include the completely complementary sequence B (3'-GAGGACACCTCTTCAGACG-5'), a center 1-mer mismatched sequence C (3'-GAGGACTCCTCTTCAGACG-5'), an end 2-mer mismatched sequence D (3'-CTGGACACCTCTTCAGACG-5'), and a completely non-complementary sequence E (3'-CCTAGTCTACAGGTCACTA-5').

The present invention will now be described in more detail with reference to the following examples and drawings.

However, these examples are given by way of illustration and not of limitation.

EXAMPLE 1

Preparation of 3'-carboxyl-5,2';5',2"-terthiophene Monomer Having Carboxyl Groups Scheme 1

Reagents and conditions; i) CuCN/DMF/4hrs/;
ii) KOH/Ethoxyethano-H₂O/5hrs/

Synthesis of 3-cyanoterthiophene: 10 mmol of 3-bromoterthiophene was refluxed in anhydrous dimethylformamide (10 ml) containing 15 mmol of copper cyanide for 4 hours. After the dark mixture was allowed to cool to room temperature it was mixed with iron chloride (10 g) in hydrochloric acid solution (20 ml, 2.0M) and maintained at 60~70° C. for 30 minutes. The organic extract was washed with hydrochloric acid solution (20 ml, 6M), distilled water, saturated sodium bicarbonate solution and aqueous sodium chloride solution to obtain a dark yellowish solid. The obtained solid was recrystallized from an organic solvent.

The product has a melting point of 83° C. and a molecular weight of 272.9736 g/mol as measured using a mass spectrometer. The structure of the product was identified through $^{13}$C NMR, $^{1}$H NMR, and IR spectrometer.

The data are as follows:

$^{1}$H NMR (CDCl$_3$): δ7.06–7.62 (m, 7H); $^{13}$C NMR δ: 106.0, 115.8, 125.6, 127.5, 126.5, 127.7, 128.0, 128.6, 128.8, 133.4, 135.0, 136.7, 145.3

Synthesis of 3'-carboxyl-5,2';5',2"-terthiophene: 10 mmol of 3-cyanoterthiophene and 17.8 mmol of potassium hydroxide were refluxed in ethoxyethanol-water (5:1) for 5 hours. The reaction mixture was acidified with an excess of hydrochloric acid solution (12M) and cooled until yellowish precipitates were formed. The precipitates were filtered, washed with distilled water and recrystallized from an organic solvent to obtain the title product as a solid. The product has a melting point of 193° C., and a molecular weight of 292.4002 g/mol as measured using a mass spectrometer. The structure of the product was identified through $^{13}$C NMR, $^{1}$H NMR, and IR spectrometer.

The data are as follows:

$^{1}$H NMR (CDCl$_3$) δ: 7.04–7.59(m, 7H), 7.59 (br s, 1H); $^{13}$C NMR δ: 125.0, 125.9, 126.9, 127.8, 128.4, 128.6, 130.2, 133.6, 135.9, 136.1, 143.8, 166.7

EXAMPLE 2

Fabrication of DNA Sensor

Figure 1:
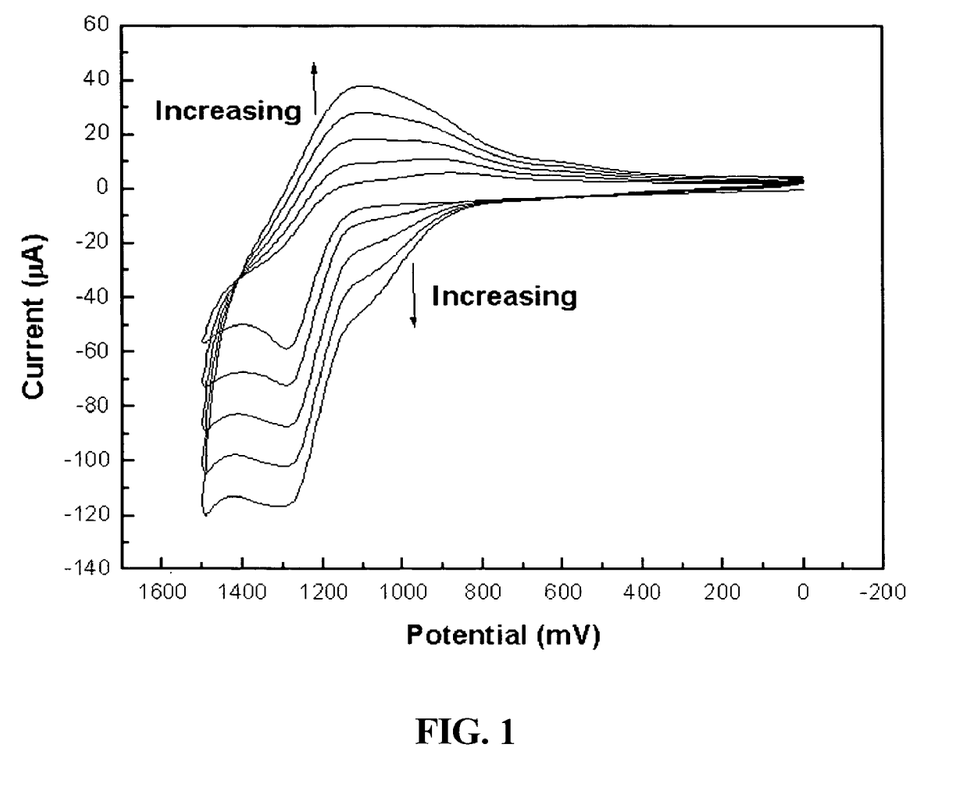
FIG. 1 is a graph showing a cyclic voltammogram pattern for electrochemical polymerization of 3'-carboxyl-5,2';5',2"-terthiophene as a monomer.

Manufacture of a modified electrode using conductive polymer of 3'-carboxyl-5,2';5',2"-terthiophene having a carboxylic group: After 3'-carboxyl-5,2';5',2"-terthiophene monomer was dissolved in acetonitrile, the monomer was polymerized on the surface of a glassy carbon and gold electrode in accordance with an electrochemical method to produce a conductive terthiophene polymer. Subsequently, the polymer was modified [FIG. 1]. Generally, in order to electrochemically produce the conductive polymer, a voltage, at which a monomer is oxidized, is applied to a solution containing the monomer, or a cyclic voltammetry method by which a polymer is produced on the surface of the electrode, is used. In the present invention, a voltage was repetitively applied in a positive (+) direction, starting at 0.0V and finishing at +1.5V. At this time, voltage scan rate was 100 mV/sec. An oxidizing current flowed between +1.1V and +1.3V, and a reducing current flowed at +1.15 V. When voltage in a range from 0.0V to +1.5V was cycled, the currents increased. Such increase in current demonstrated that the conductive polymer was produced on the surface of electrode. The number of voltage cycles varied from 1 to 50. FIG. 1 shows cyclic voltammogram pattern at 5 voltage cycles. The conductive polymer produced on the surface of electrode had a reddish brown color.

Figure 2:
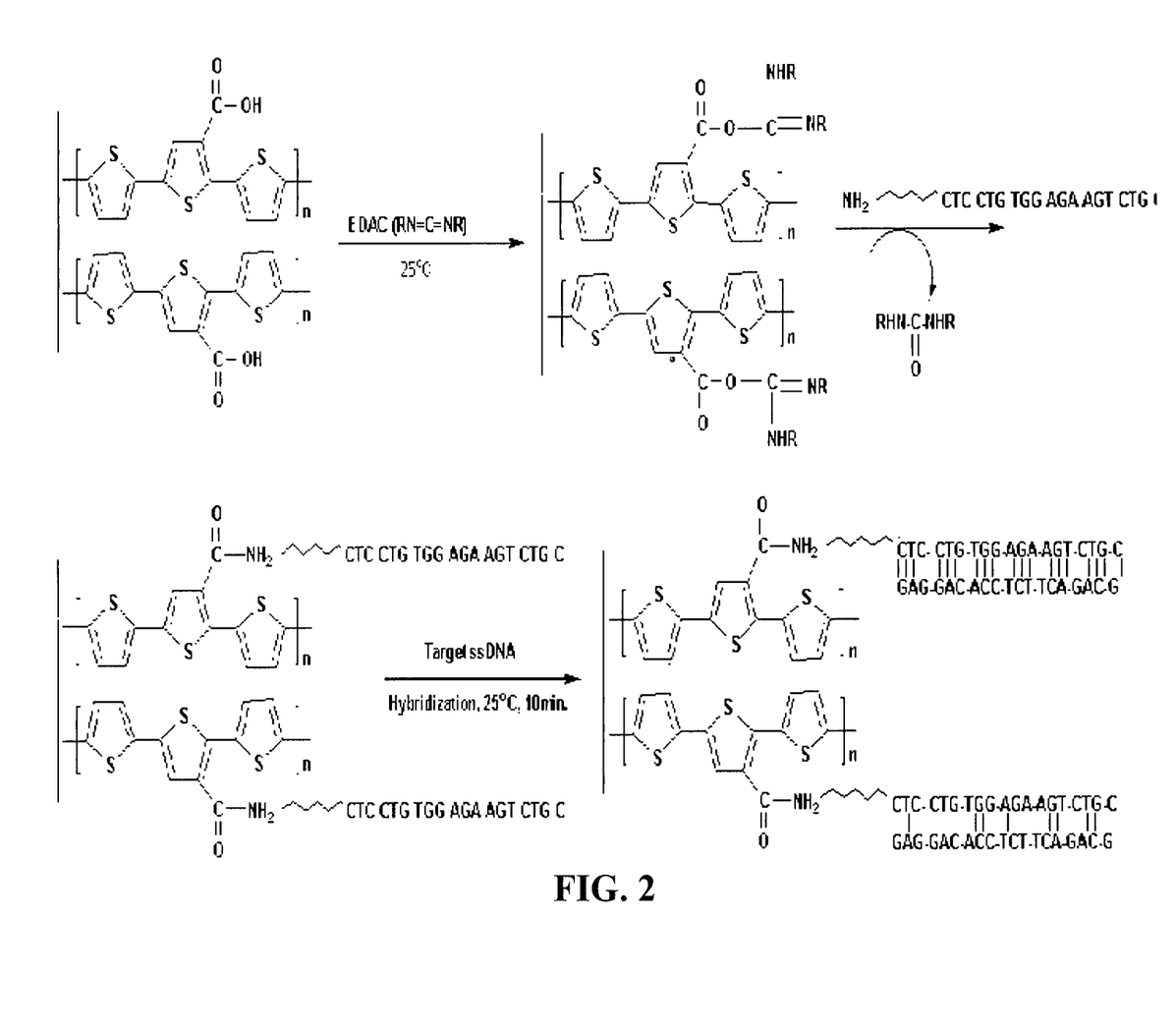
FIG. 2 is a scheme showing an immobilization of a probe oligonucleotide and a hybridization of a target sequence.

Immobilization of probe oligonucleotide: A probe oligonucleotide sequence (NH$_2$—C$_6$-5'-CTCCTGTG-GAGAAGTCTGC-3'), which is amine-modified at its 5'-end using 1-ethyl-3-(3-dimethylaminopropyl)carbodiimide (EDAC), was immobilized onto an electrode. EDAC used herein is a catalyst to combine an amino group to a carboxyl group. The conductive polymer electrochemically produced on the surface of the electrode, in accordance with the procedure of FIG. 1, has carboxyl groups. The conductive polymer was combined to a probe oligonucleotide having an amino-modified 5'-end to fabricate a DNA sensor. The electrode coated with the conductive polymer, which is produced in accordance with the procedure of FIG. 1, was immersed in a phosphate buffer (pH 7.4) containing EDAC (10 mg/mL) and the probe oligonucleotide having an amino-modified 5'-end (11 M) and then reacted at room temperature for 10 hours to fabricate a DNA sensor. In the DNA sensor, carboxylic acid of the conductive polymer was bound with amino group of the probe oligonucleotide. In a similar manner, the binding of a particular disease-associated probe DNA (or oligonucleotide) with the conductive polymer will lead to development of disease-associated DNA detection sensors.

EXAMPLE 3

Impedance Measurement

Figure 3A:
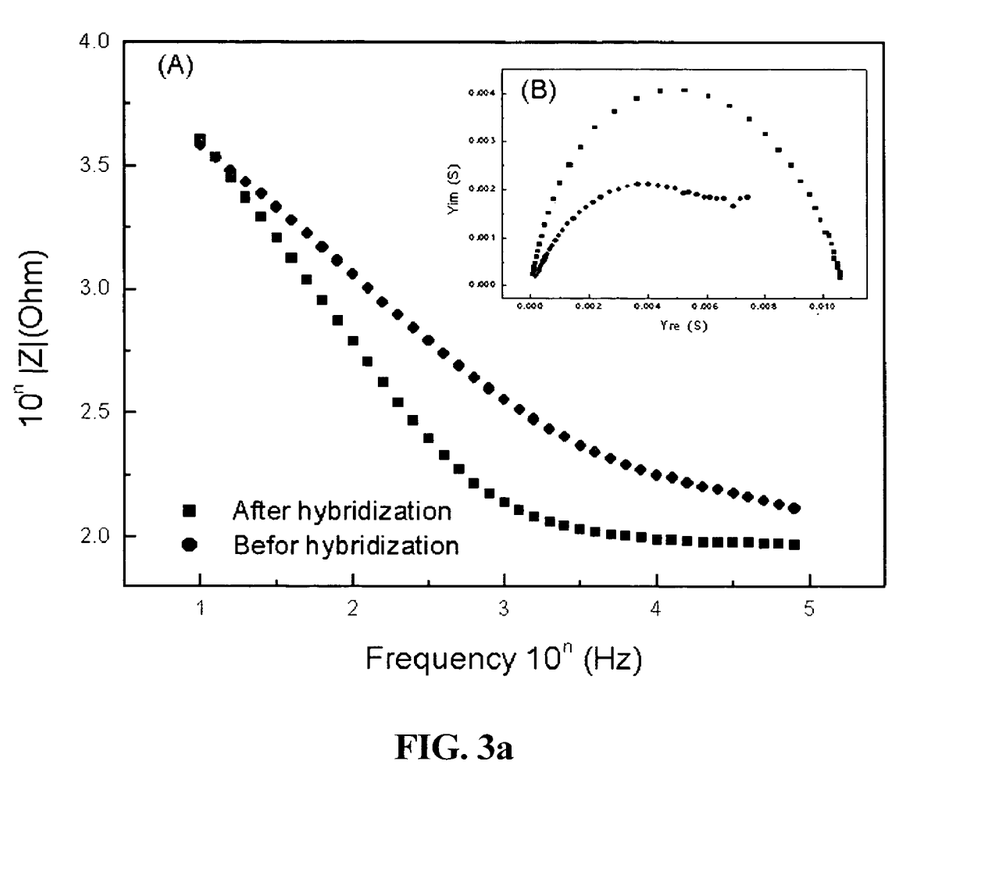
FIG. 3a is a graph showing changes in the impedance(A) and admittance(B) before and after hybridization on an open circuit voltage in a phosphate buffer (pH 7.4) at room temperature.

Impedance measurement was performed before and after hybridizations with target DNA sequences in a phosphate buffer. The target DNA base sequence include the completely complementary sequence B (3'-GAGGACACCTCT-TCAGACG-5'), a center 1-mer mismatched sequence C (3'-GAGGACTCCTCTTCAGACG-5'), an end 2-mer mismatched sequence D (3'-CTGGACACCTCTTCAGACG-5'), and a completely non-complementary sequence E (3'-CCTAGTCTACAGGTCACTA-5') [FIGS. 3a to 3c]. FIG. 3a shows impedances of the probe oligonucleotide (a single-stranded DNA sequence immobilized onto the conductive polymer on the electrode surface) in the frequency range from 100 kHz to 10 Hz in a phosphate buffer (pH 7.4) containing 0.75M NaCl after the probe oligonucleotide was immobilized onto the electrode surface and impedances were measured under the same conditions as above after the electrode was reacted with target DNA sequences (single-stranded DNA sequences to be reacted with the probe) for 30 minutes. Following reacting with the target DNA sequences, impedance values sharply decreased (see, (A) in FIG. 3a). It can also be seen that there were significant differences in admittance measurement before and after hybridization (see, (B) in FIG. 3a). As shown in FIG. 3a, resistance (y-axis) dropped after hybridization. This means that conductivity increased after hybridization.

Figure 3B:
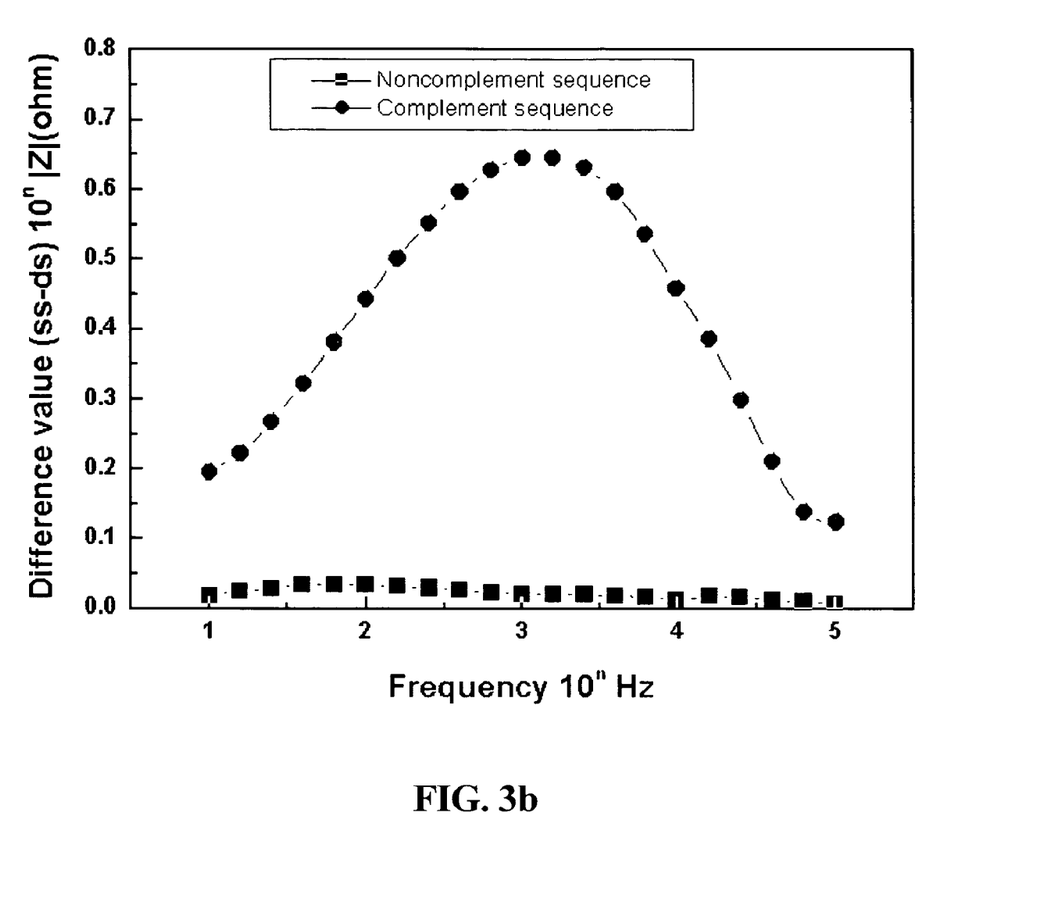
FIG. 3b is a graph showing differences in the impedance before and after hybridization with a noncomplementary target sequence E and a complementary target sequence B, respectively.

After hybridizing with the non-complementary target sequence E, a graph showing differences between log values of the measured impedances before and after hybridization was plotted (see, FIG. 3b). As shown in FIG. 3b, the differences were close to zero. This suggests that since no hybridization occurred there was no change in impedances after hybridization. However, when the electrode was again hybridized with the completely complementary target DNA sequence B, there were significant differences (FIG. 3b). This suggests that hybridization occurred and thus there was significant change in impedance after hybridization. Accordingly, it was possible to distinguish the completely complementary target DNA sequence B from the completely non-complementary sequence E.

After hybridizing the center 1-mer mismatched sequence C (see, upper graph in FIG. 3c) and the end 2-mer mismatched sequence D (see, lower graph in FIG. 3c), a graph showing differences between log values of the measured impedances before and after hybridization was plotted. The results were obtained through 3 repetitive measurements for each sequence. After hybridization, impedance change was slight, but comparable to the completely complementary sequence (Sequence B). Accordingly, it was possible to distinguish the completely complementary sequence from the mismatched sequences through impedance measurement.

Figure 3C:
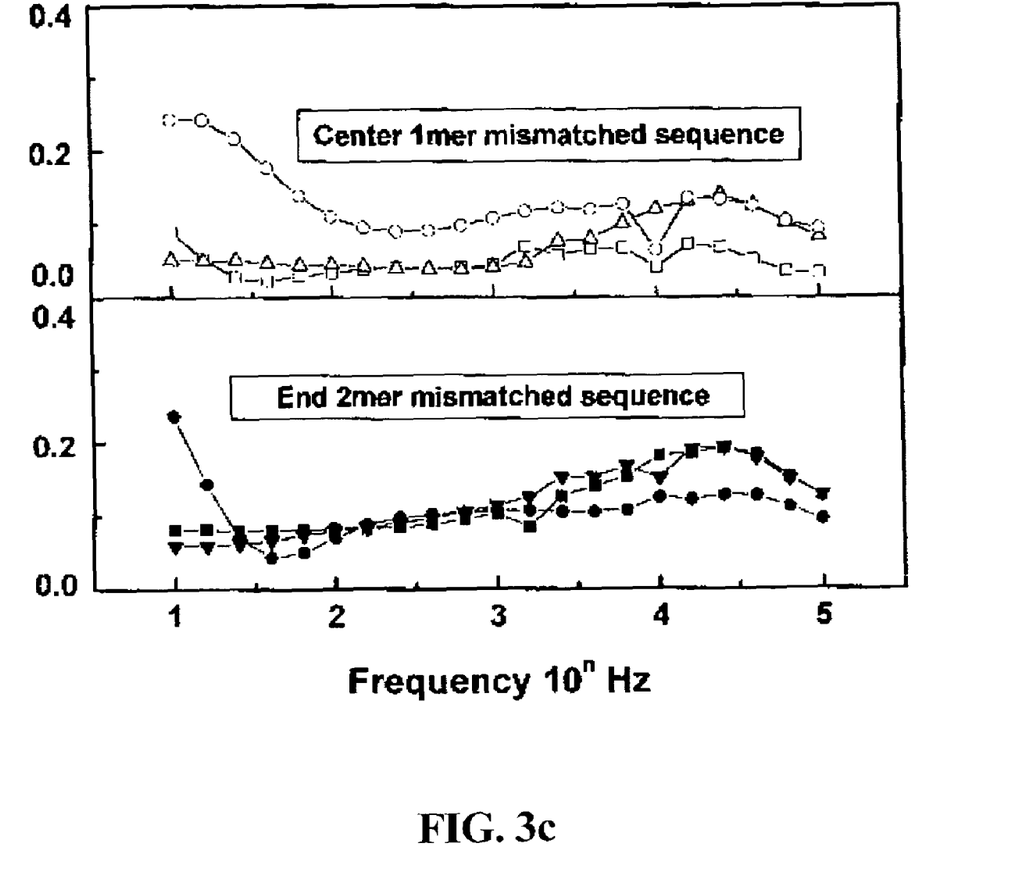
FIG. 3c is a graph showing differences in the impedance before and after hybridizations with a center base-mismatched sequence and an end base-mismatched sequence, respectively.

As shown in FIG. 3, impedance change was greatest at 1 kHz, following hybridization with the target DNA sequences and the process for detecting DNA hybridization according to the present invention had an excellent selectivity to mismatched base sequences, compared to conventional detecting methods. Accordingly, the process for detecting DNA hybridization according to the present invention can simply identify whether or not hybridization is done through impedance measurement at a certain frequency, for example 1 kHz.

Experimental Results:

Selectivity depends on the ability to distinguish the completely complementary sequence from mismatched sequences. In the present invention, the degree of hybridization was evaluated by comparing log values of the measured impedances before and after hybridization at 1 kHz. From the evaluated degree of hybridization, selectivity to a particular sequence can be seen.

The results are shown in Table 1 below.

TABLE 1

| Oligonucleotide Sequences[b] | |Z|/10 n Ohm | Degree of Hybridization (%)[c] |
|---|---|---|
| Complementary (Sequence B)<br>3'-GAG-GAC-ACC-TCT-TCA-GAC-G-5 | 0.7 ± 0.05 | 100% |
| 1-base mismatched sequence (Sequence C)<br>3'-GAG-GAC-TCC-TCT-TCA-GAC-G-5' | 0.1 ± 0.05 | 14.3% |
| End 2-base mismatched sequence (Sequence D)<br>3'-CTG-GAC-ACC-TCT-TCA-GAC-G-5' | 0.1 ± 0.05 | 14.3% |
| Non-complementary (Sequence E)<br>3'-CCT-AGT-CTA-CAG-GTC-ACT-A-5' | 0.0 ± 0.05 | 0% |

[a]probe oligonucleotide of $NH_2$-$C_6$-5'-CTC-CTG-TGG-AGA-AGT-CTG-C-3 was immobilized onto the polyterthiophene-modified glass carbon electrode.
[b]Concentration: 110 nmol in 10 ml
[c]denotes the amount of oligonucleotides combined to the probe immobilized onto the modified electrode.

Comparison with Known Data:

In 1992, Okahata et al. performed hybridization detection on various 10-mer nucleotides using QCM. In the experiment, the end 2-mer mismatched sequence showed a hybridization of 92%, and the center monomer mismatched sequence showed a hybridization of about 30% (see, Table 2). On the other hand, as shown in Table 1, the process for detecting hybridization according to the present invention showed a hybridization of 14.3%. Accordingly, it can be seen that hybridization detection using impedance can selectively distinguish hybridizations with target DNA sequences. The degree of hybridization between a probe-immobilized QCM and various 10-mer nucleotides at 25° C. is shown in Table 2 below.

TABLE 2

| Nucleotides[b] | Δm/ng | Degree of hybridization (%) |
|---|---|---|
| 3'd<u>CCCTTAAGCA</u>5' | 380 ± 10 | 100 |
| 3'd<u>CCCTTAA</u>GGG5' | 350 ± 10 | 92 |
| 3'dTG<u>CTTAAGCA</u>5' | 350 ± 10 | 92 |
| 3'd<u>CCC</u>TA<u>AAGCA</u>5' | 125 ± 10 | 31 |
| 3'd<u>CCC</u>TG<u>AAGCA</u>5' | 100 ± 10 | 26 |
| 3'd<u>C</u>TG<u>C</u>T<u>A</u>CGGG5' | 0 | 0 |
| 3'dAG<u>CC</u>GT<u>A</u>C<u>CC</u>5' | 0 | 0 |

[a]HS-5'Pd<u>GGGAATTCGT</u>3' was immobilized onto QCM in a relatively large amount (847 ng, 280 pmol, ca. 65% of electrode coating) in order to obtain high sensitivity to oligonucleotides having a relatively low molecular weight, compared to M13 phage DNA,
[b]Concentration: 400 ng in 10 ml (130 pmol). The underlines denote sequences complementary to the probe.
[c]denotes the amount of oligonucleotides combined to the probe immobilized on QCM.

As can be seen from the foregoing, according to the present invention, a process capable of detecting DNA hybridization using impedance change, without the use of any indicator, is provided. Therefore, small-sized sensor systems which measure impedance in a particular frequency range can be fabricated. The systems are applicable to portable sensors for identifying DNA sequence hybridization for clinical examination and disease diagnosis.

Further, the process for detecting DNA hybridization according to the present invention has an excellent selectivity of complementary sequences to mismatched sequences.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

What is claimed is:

1. 3'-carboxyl-5,2';5',2"-terthiophene represented by the following formula 1:

2. A method for preparing 3'-carboxyl-5,2';5',2"-terthiophene according to claim 1 comprising the steps of treating 3-bromoterthiophene with copper cyanide (CuCN) to obtain 3-cyanoterthiophene, and hydrolyzing the obtained 3-cyanoterthiophene in KOH-ethoxyethanol.

3. A functionalized conductive terthiophene polymer of the following formula 3 produced in an electrochemical method which synthesizes the polymer using 3'-carboxyl-5, 2';5',2"-terthiophene as a monomer on the surface of electrode in accordance with cyclic voltammetry method:

4. A process for detecting DNA hybridization comprising the steps of:

dissolving 3'-carboxyl-5,2';5',2"-terthiophene in a non-aqueous solvent;

producing the conductive terthiophene polymer having carboxylic groups on the surface of electrode in an electrochemical method and modifying the polymer;

immobilizing a probe DNA amino-modified at its 5'-end using 1-ethyl-3-(3-dimethylaminopropyl)carbodiimide (EDAC) onto the polymer; and measuring impedance before and after DNA hybridization.

5. The process for detecting DNA hybridization according to claim 4, wherein the impedance measurement is performed at a frequency of 1 kHz.

6. A method for manufacturing a probe DNA comprising the steps of:

binding an alkyl group having from 3 to 10 carbon atoms to the 5'-end of DNA having base sequences with a certain length; and combining an amino group to the alkyl group using 1-ethyl-3-(3-dimethylaminopropyl) carbodiimide (EDAC) to modify the 5'-end into an amino group.

7. The method for manufacturing a probe DNA according to claim 6, wherein the DNA is a 19-mer oligonucleotide, and the alkyl group has 6 carbon atoms.

* * * * *

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide prob

<400> SEQUENCE: 1
ctcctgtgga gaagtctgc                                              19

<210> SEQ ID NO 2
<211> LENGTH: 19
<212> TYPE: DNA
<213> ORGANISM: Artificial Sequence
<220> FEATURE:
<223> OTHER INFORMATION: target DNA complementary to the probe

<400> SEQUENCE: 2
gaggacacct cttcagacg                                              19

<210> SEQ ID NO 3
<211> LENGTH: 19
<212> TYPE: DNA
<213> ORGANISM: Artificial Sequence
<220> FEATURE:
<223> OTHER INFORMATION: target DNA complementary to the probe

<400> SEQUENCE: 3
gaggactcct cttcagacg                                              19

```
<210> SEQ ID NO 4
<211> LENGTH: 19
<212> TYPE: DNA
<213> ORGANISM: Artificial Sequence
<220> FEATURE:
<223> OTHER INFORMATION: target DNA complementary to the probe

<400> SEQUENCE: 4
ctggacacct cttcagacg                                              19

<210> SEQ ID NO 5
<211> LENGTH: 19
<212> TYPE: DNA
<213> ORGANISM: Artificial Sequence
<220> FEATURE:
<223> OTHER INFORMATION: target DNA non-complementary to the probe

<400> SEQUENCE: 5
cctagtctac aggtcacta                                              19

<210> SEQ ID NO 6
<211> LENGTH: 10
<212> TYPE: DNA
<213> ORGANISM: Artificial Sequence
<220> FEATURE:
<223> OTHER INFORMATION: oligonucleotide probe

<400> SEQUENCE: 6
gggaattcgt                                                        10

<210> SEQ ID NO 7
<211> LENGTH: 10
<212> TYPE: DNA
<213> ORGANISM: Artificial Sequence
<220> FEATURE:
<223> OTHER INFORMATION: target DNA

<400> SEQUENCE: 7
cccttaagca                                                        10

<210> SEQ ID NO 8
<211> LENGTH: 10
<212> TYPE: DNA
<213> ORGANISM: Artificial Sequence
<220> FEATURE:
<223> OTHER INFORMATION: target DNA

<400> SEQUENCE: 8
cccttaaggg                                                        10

<210> SEQ ID NO 9
<211> LENGTH: 10
<212> TYPE: DNA
<213> ORGANISM: Artificial Sequence
<220> FEATURE:
<223> OTHER INFORMATION: target DNA

<400> SEQUENCE: 9
tgcttaagca                                                        10

<210> SEQ ID NO 10
<211> LENGTH: 10
<212> TYPE: DNA
<213> ORGANISM: Artificial Sequence
<220> FEATURE:
```

```
-continued

<223> OTHER INFORMATION: target DNA

<400> SEQUENCE: 10
ccctaaagca                                                              10

<210> SEQ ID NO 11
<211> LENGTH: 10
<212> TYPE: DNA
<213> ORGANISM: Artificial Sequence
<220> FEATURE:
<223> OTHER INFORMATION: target DNA

<400> SEQUENCE: 11
ccctgaagca                                                              10

<210> SEQ ID NO 12
<211> LENGTH: 10
<212> TYPE: DNA
<213> ORGANISM: Artificial Sequence
<220> FEATURE:
<223> OTHER INFORMATION: target DNA

<400> SEQUENCE: 12
ctgctacggg                                                              10

<210> SEQ ID NO 13
<211> LENGTH: 10
<212> TYPE: DNA
<213> ORGANISM: Artificial Sequence
<220> FEATURE:
<223> OTHER INFORMATION: target DNA

<400> SEQUENCE: 13
agccgtaccc                                                              10
```